United States Patent [19]

Moioli

[11] 4,000,656

[45] Jan. 4, 1977

[54] APPARATUS FOR DESIGNING AND TESTING PROPER VALUES OF PARAMETERS RELATING TO SUPPORTING HYDRODYNAMICALLY LUBRICATED BEARING JOURNALS

[76] Inventor: Alessandro Moioli, Via Fornaci, 2, Nembro (Bergamo), Italy, 24027

[22] Filed: Dec. 24, 1975

[21] Appl. No.: 644,298

[30] Foreign Application Priority Data

Jan. 10, 1975   Italy .................................. 2902/75

[52] U.S. Cl. ............................... 73/432 R; 73/10; 73/64
[51] Int. Cl.² ....................................... G01N 19/08
[58] Field of Search ............. 73/10, 58, 432 R, 64, 73/344, 345, 343 R; 324/65 R

[56] References Cited

UNITED STATES PATENTS

| | | | |
|---|---|---|---|
| 1,989,627 | 1/1935 | Sage | 73/10 |
| 2,808,563 | 10/1957 | Hornbostel | 73/10 |
| 3,375,699 | 4/1968 | Lindeman | 73/10 |

*Primary Examiner*—Donald O. Woodiel

[57] ABSTRACT

Apparatus for designing and determining parameters for supporting hydrodynamically lubricated bearing journals, wherein a device for applying a load to a shaft is associated with a shaft mounted on bushings carried by ball joints, the shaft and bushings being electrically insulated from the remainder of the apparatus, and detecting devices being also provided which are responsive at determined locations to changes in parameters, such as supporting pressure, temperature, separation between shafts and bushings, and the like.

7 Claims, 3 Drawing Figures

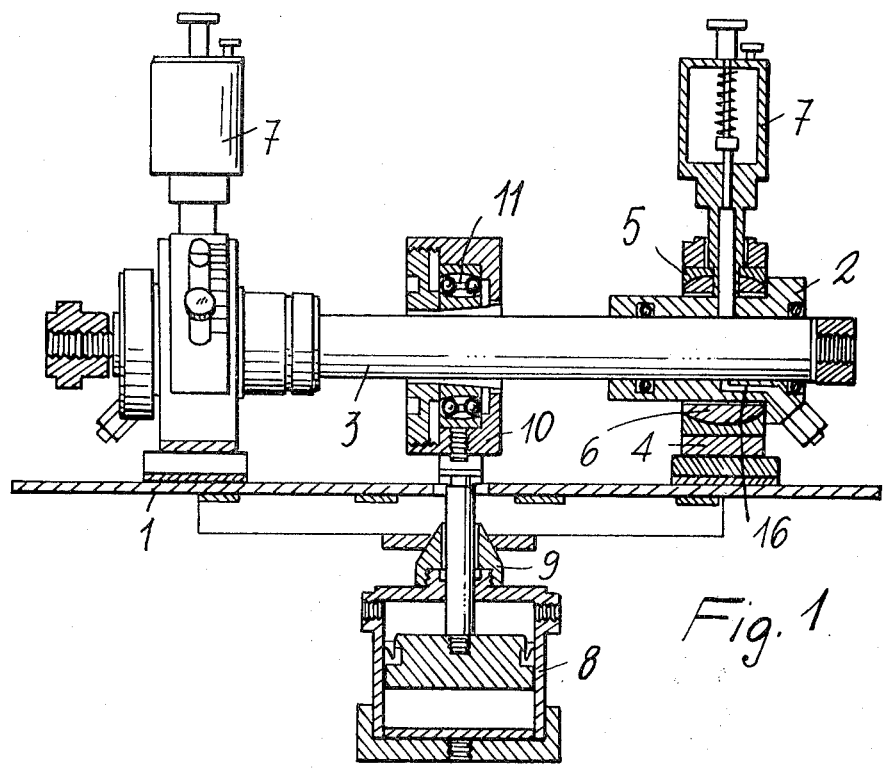
Fig. 1
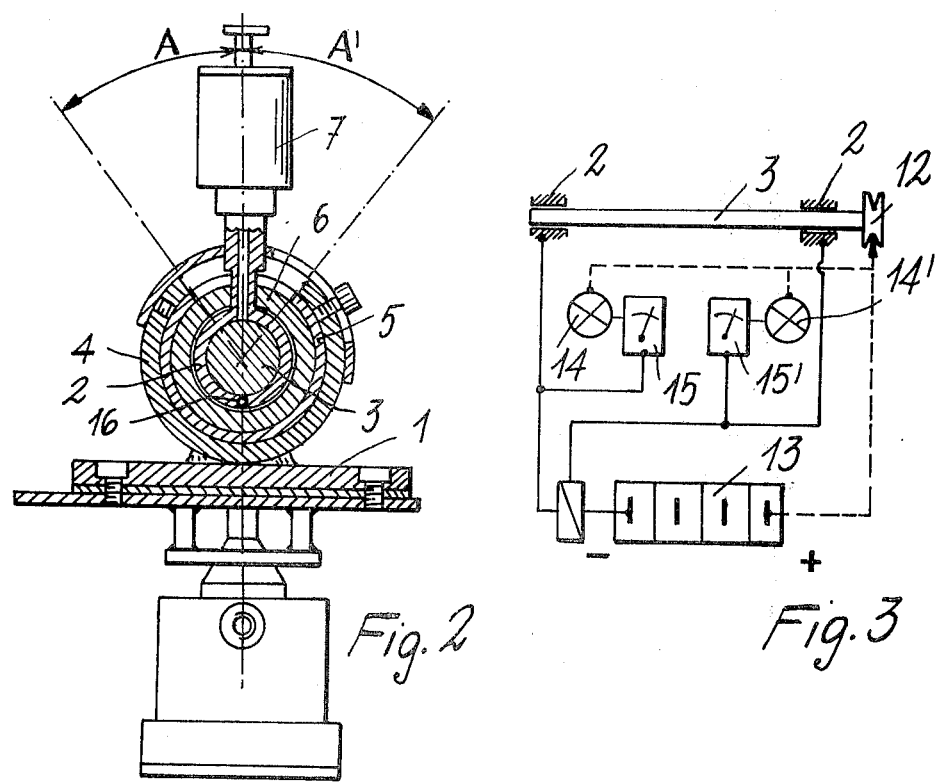
Fig. 2
Fig. 3

APPARATUS FOR DESIGNING AND TESTING PROPER VALUES OF PARAMETERS RELATING TO SUPPORTING HYDRODYNAMICALLY LUBRICATED BEARING JOURNALS

This invention relates to an apparatus for accurately establishing of proper rates of parameters involved in supporting hydrodynamically lubricated bearing journals, particularly an apparatus for verifying empirical rates calculated by a designer on the ground of tables, curves and the like.

As well known, a designer for a rotary kinematic coupling (formed of bearing journal and bushing) is mostly compelled, as far as lubrication is concerned, to rely on tables, curves and calculation coefficients, including empirically drawn orientative rates and therefore not quite corresponding to reality. Such rates drawn from general experiences can never properly meet the requirements for a specific coupling which, as such, has well defined operating characteristics and qualifications.

Said parameters comprise, for example, specific or rated load; speed; radial play; viscosity; journal roughness; bushing roughness; supporting pressure; separation; and temperature. Among these several parameters, making up the unknown values for the problem to be solved, a designer would first set some of the values or rates of interest, such as specific or rated load, speed, etc., and derive therefrom the other rates on the ground of tables and the like, which, as above mentioned, are sometimes well out of reality.

It is the object of the present invention to provide a suitable apparatus for showing and verifying the hydrodynamic supporting laws, on which apparatus particularly a change in said main parameters can be provided. Particularly, the apparatus will be capable of simultaneously controlling the supporting pressure and the well known separation between two members moving relatively to each other as a lubricant film is formed therebetween. In brief, taking advantage of the resulting capability of changing the parameters affecting the operating conditions in a lubricated cylindrical coupling, said apparatus affords the setting up of a methodical research study for the proper values of all of the parameters being involved in hydrodinamic journal support to provide from the kinematic or lower pair under examination a proper operating condition, as well as the highest mechanical efficiency and preservation of involved surfaces from sliding wear.

According to the invention, this is accomplished by an apparatus for the above mentioned objects, having a base carrying thereon two bearings for a respective independent bushing, and a pin or shaft mounted in said bushings, characterized in that a device is provided for applying the load to said shaft, and that said bushings are carried in said bearings by means of ball joints, and that at least one detecting device is associated with said pair comprising each bushing and shaft, this detecting device being responsive to separation between pin and bushing and/or changes in temperature, thickness of lubricating film and similar parameters involved in lubrication.

These and further objects, features, details and advantages of an apparatus according to the invention will become more apparent to those skilled in the art from the description of an embodiment given by way of unrestrictive example in connection with the accompanying drawings, in which:

FIG. 1 is a longitudinal, partly sectional view showing the mechanical unit of the present apparatus;

FIG. 2 is an end sectional view of the apparatus shown in FIG. 1; and

FIG. 3 is an exemplary electric diagram for displaying the hydrodynamic separation effect.

Referring now to the drawings, reference numeral 1 designates a base having bearings mounted therein for accomodating on either side a bushing 2 which, in turn, has a shaft 3 mounted therein. Each of the bushings, forming together with shaft 3 the two experimental pairs electrically insulated from the remainder of the apparatus, rest on bearing 4, ball joints 5,6 being mounted on the latter enabling self-alignment and radial travel A and A' of the bushing surface involved by the supporting pressures even as the pin is moving. As it will be seen on the drawings, each of the bushings have a respective oiler or lubricator 7 with a communicating through hole and associated sealing plug. The apparatus also comprises a device for load application to shaft 3, which device includes a hydraulic cylinder 8 which, through a bevel gear 9 and tie-rod integral with the piston of said cylinder, is effective on the housing 10 of a self-aligning ball bearing 11 ensuring a constant application of the load in a vertical direction on rotating shaft 3. Obviously, although not shown herein, a variable speed control means would be provided for rotably driving said shaft 3.

Thus, upon rotably driving said shaft through the driving means, not shown, and setting up the desired specific or rated load by means of assembly 8, 9, 10 and 11, as favourable operating conditions are attained, a lubrication film will be built up between each bushing 2 and shaft 3, and according a separation between bushings and shaft, the lubricant being supplied through elements 7, as above stated. To verify and control the proper value or rate for said separation between bushing and pin or shaft, use is made of a circuit, such as that shown in FIG. 3. In that circuit, reference numeral 12 designates a brush commutator connected to the positive pole of a battery, of which the negative pole is connected to bushing 2, preferably with a separated pilot lamp 14 and 14' and a separated milliamepereme-ter 15 and 15' for each of bushings 2. As the oil film varies in thickness, that is as separation varies between each of bushings 2 and pin or shaft 3, pilot lamp 14 for each of the bushings will be lit and its intensity will be increased as separation varies with a corresponding increase in the displacement of the pointer of each amperemeter 15 or 15'. Through such a circuit, herein quite diagramatically shown, the change in separation between bushing and pin or shaft can therefore be signalled and indicated, whereby the proper use value can be provided. similarly, the above described apparatus can be associated with other electric or electronic circuits for determining other parameters, such as temperature, viscosity, oil film thickness measurement and the like, which have to be matched to one another or combined, so that the resultant of the values or rates thereof is the proper one.

As mentioned in the foregoing, bushings 2 are carried on said ball joints allowing, in addition to bushing self-alignment also rotation in a radial direction of said bushing with a movement or travel across the entire supporting zone, so that the radial diagram for the supporting pressures can be exactly obtained, in addition to longitudinal pressures obtainable without the provision of ball joints, through accommodation of survey location along said bushing, provided by hole 16.

Although the invention has been described in connection with a particular embodiment thereof, the invention is not restricted to the constructive details shown and/or described, but comprises all of changes and equivalents thereof. Particularly, on the ground of the present embodiment, other electric and/or electronic circuits can be applied to the present apparatus for taking other parameters involved in lubrication.

Therefore, any additions and/or modifications made by those skilled in the art on the ground of the present inventive concept would be within the scope of the invention.

What I claim is:

1. An apparatus for designing and testing the proper values of parameters relating to supporting hydrodynamically lubricated bearing journals, comprising:
    a base;
    two independent bushings mounted on said base;
    a shaft mounted in said bushings;
    a device coupled to said shaft between said bushings for load application to said shaft, said shaft and bushings being electrically insulated from the remainder of the apparatus;
    ball joints and bearings rockably mounting said bushings for self-alignment with said shaft; and
    at least one detecting device associated with each of the bushings and said shaft, said detecting device being adapted to indicate the value of a selected parameter.

2. An apparatus according to claim 1, wherein said detecting location for the supporting pressure comprises a hole which is properly proportioned and positioned within the bushing and communicating with a channel leading to a pressure gauge, with detection capability even during shaft rotation.

3. An apparatus according to claim 1, wherein said shaft includes a brush commutator, and said device for detecting separation between the shaft and bushing includes, for each of the bushings, a pilot lamp provided with an ammeter and connected to the bushing and negative pole of a battery, of which the positive pole is connected to said brush commutator associated with said rotating shaft.

4. An apparatus according to claim 1, wherein said device for load application to the rotating shaft comprises:
    a bearing about said shaft;
    a pressure member bearing on said bearing; and
    a hydraulic cylinder acting on said pressure member carried on said shaft through the interposition of said bearing.

5. An apparatus according to claim 1, wherein said detecting device is responsive to separation between said shaft and said bushing.

6. An apparatus according to claim 1, wherein said detecting device is responsive to the temperature at the bushing.

7. An apparatus according to claim 1, wherein said detecting device is responsive to the supporting pressure of said bushing at determined locations along said bushings.

* * * * *